United States Patent [19]

Kladders

[11] Patent Number: 4,889,114
[45] Date of Patent: Dec. 26, 1989

[54] POWDERED PHARMACEUTICAL INHALER

[75] Inventor: Heinrich Kladders, Ingelheim am Rhein, Fed. Rep. of Germany

[73] Assignee: Boehringer Ingelheim KG, Ingelheim am Rhein, Fed. Rep. of Germany

[21] Appl. No.: 69,316

[22] Filed: Jul. 2, 1987

Related U.S. Application Data

[63] Continuation of Ser. No. 905,693, Sep. 9, 1986, abandoned, which is a continuation of Ser. No. 681,008, Dec. 13, 1984, abandoned.

[30] Foreign Application Priority Data

Dec. 17, 1983 [DE] Fed. Rep. of Germany ....... 3345722

[51] Int. Cl.⁴ ........................................... A61M 15/06
[52] U.S. Cl. ................... 128/203.15; 604/58
[58] Field of Search ................... 128/203.15; 604/58

[56] References Cited

U.S. PATENT DOCUMENTS

| | | |
|---|---|---|
| 2,569,720 | 10/1951 | Jesnig ............................. 128/203.15 |
| 2,722,935 | 11/1955 | Thompson et al. ................... 104/58 |
| 3,507,277 | 4/1970 | Altounyan et al. ............ 128/203.15 |
| 3,837,341 | 9/1974 | Bell ................................. 128/203.15 |
| 3,906,950 | 9/1975 | Cocozza ......................... 128/203.15 |
| 3,918,451 | 11/1975 | Steil ................................ 128/703.15 |
| 3,991,761 | 11/1976 | Cocozza ......................... 128/203.15 |
| 3,999,751 | 4/1976 | Birch et al. ..................... 128/203.15 |
| 4,069,819 | 1/1978 | Valentini et al. .............. 128/203.15 |
| 4,338,931 | 7/1982 | Cavazza ......................... 128/203.15 |

Primary Examiner—Max Hindenburg
Assistant Examiner—Reichle: K. M.
Attorney, Agent, or Firm—Felfe & Lynch

[57] ABSTRACT

An inhaler for the inhalation of powdered pharmaceutical compositions from capsules. The inhaler comprises a chamber for receiving the capsules, which chamber has a greater internal width and a greater length than the diameter and length, respectively, of the capsule and which chamber comprises at one narrow end an air inlet and at the other end an air outlet, so that during inhalation through the inhaler the capsule is set in vibration.

3 Claims, 1 Drawing Sheet

U.S. Patent     Dec. 26, 1989     4,889,114

# POWDERED PHARMACEUTICAL INHALER

This is a continuation of copending application Ser. No. 905,693, filed Sept. 9, 1986, now abandoned; which, in turn, is a continuation of application Ser. No. 681,008, filed Dec. 13, 1984, now abandoned.

FIELD OF THE INVENTION

This invention is directed to an inhaler. More particularly, this invention is directed to an inhaler for the inhalation of powdered pharmaceutical preparations from capsules.

BACKGROUND OF THE INVENTION

Inhalers for the inhalation of pharmaceutical preparations packed in capsules wherein the capsules are moved during the inhalation, are already known. An inhaler of this type is known, for example, from German Offenlegungsschrift 1,566,604. The inhaler described therein comprises a device for receiving the capsules which has propeller-like wings and is mounted coaxially with the longitudinal axis of the apparatus. During inhalation, the device with the capsule is set rotating by the apparatus.

Whereas in the inhaler described above the pharmaceutical capsule is fixed in a movable part of the apparatus and is moved therewith, French patent application Ser. No. 2,146,202 describes an inhalation apparatus with a flat cylindrical chamber in which only the capsule itself moves. The capsule, which is opened at its ends, is driven by air flowing tangentially inwards and rotates about its transverse axis during inhalation.

Both of these known inhalers have the major disadvantage that the pharmaceutical composition is expelled unevenly. Some capsules are emptied virtually entirely while others still contain considerable amounts of pharmaceutical preparation after the inhalation process. This is the case particularly with very finely divided (micronized) pharmaceutical preparations.

OBJECTS OF THE INVENTION

It is an object of the invention to provide an inhaler.

It is also an object of the invention to provide an inhaler for the inhalation of powdered pharmaceutical preparations from conventional capsules.

It is a further object of the invention to provide an inhaler for the inhalation of powdered pharmaceutical preparations from capsules in which opened capsules are vibrated by an air current during the inhalation.

These and other objects of the invention will become more apparent from the description below.

DETAILED DESCRIPTION OF THE INVENTION

Figure 1:
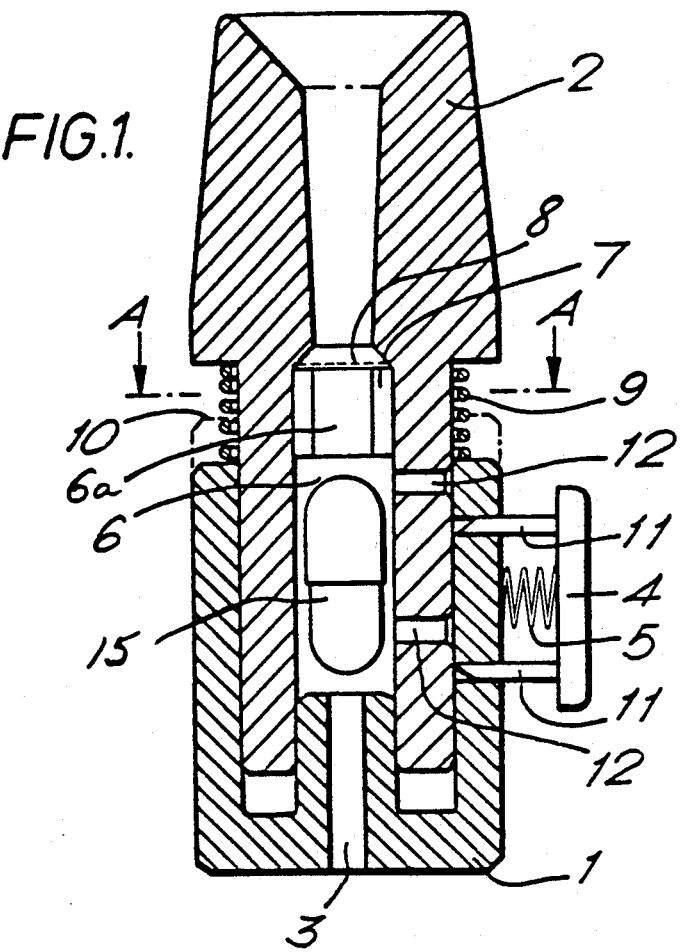
FIG. 1 represents a longitudinal, cross-sectional view of an embodiment of the invention.

The inhaler according to the invention not only permits a more reliable expulsion of the pharmaceutical preparation with a low standard deviation, but it also has the additional advantage of better fragmentation. In fact, the micronized pharmaceutical preparations in the capsules have a tendency to form clumps. These clumps are therapeutically undesirable as the pharmaceutical preparation should be as finely divided as possible. Whereas only inadequate fragmentation is achieved with the known inhalers, the clumps are largely destroyed when the inhaler according to the invention is used.

The inhaler according to the invention has a chamber for receiving the capsules, the internal width of this chamber being from about 1.1 to 2.5, preferably from about 1.1 to 2.2, more particularly from about 1.2 to 1.6, times the size of the diameter of the capsule while the length of this chamber is from about 1.02 to 2, preferably from about 1.04 to 1.8, more particularly from about 1.1 to 1.6, times the length of the capsule. The internal width of the chamber must be less than the length of the capsule.

The capsules themselves normally consist of hard gelatine. The length to width (diameter) ratio of such capsules is generally from about 1.5:1 to 4:1, preferably from about 2:1 to 3:1. Typically such capsules are from about 1 to 3 cm, especially from about 1.5 to 2.5 cm, in length.

An air inlet aperture is appropriately provided in the center of the base of the chamber. If the air inlet aperture is not in the center of the base of the chamber, it must be arranged so that the cap of the capsule can close it off as will be appreicated from the description below of the method of operation. The aperture is smaller than the diameter of the capsule, its diameter being preferably from about 0.05 to 0.5 times the internal width of the chamber. The aperture is preferably circular.

The chamber is conveniently cylindrical. However, it may also have an oval or polygonal cross-section.

An air outlet is located in that part of the chamber which is opposite the air inlet aperture and must be of a configuration such that the capsule is not sucked against the outlet aperture during inhalation so as to close it off. There are various possible ways to prevent the outlet aperture from being closed off by the capsule. For example, the wall of the capsule chamber opposite the air inlet aperture may be in the form of a perforated plate, or projecting parts may be provided which are sufficiently close together for their spacing to be less than the diameter of the capsule. Furthermore, one or more aperture may be provided as outlet apertures at the upper end of the side walls. The total cross-section available for the outflow of air from the capsule chamber is advantageously greater than the air inlet aperture cross-section to ensure that the air charged with the pharmaceutical substance can flow out with as little interference as possible.

The air mixed with pharmaceutical substance in the chamber is conveyed to the mouth of the user by means of a mouthpiece. The mouthpiece, which is generally tubular, possibly somewhat flattened, may be mounted axially or at an angle to the axis of the chamber or may be offset laterally from the axis of the chamber.

The inhaler according to the invention preferably consists of at least two parts which are held together by a screw or pushed-in connection. The parts are shaped so that when they are taken apart, the chamber is opened and the capsule can be inserted or removed. If the chamber is laterally mounted, an axially movable cover may be provided which opens or closes the chamber dependent upon its position and which, in the closed position, forms part of the side walls of the chamber. If the part of the inhaler containing the chamber is cylindrical, the cover of the chamber may also be in the form of a sleeve which is rotatable about the axis of the inhaler and which, in a certain position, enables the capsule to be put in or taken out.

For the inhalation process. the capsule must be perforated at two points, one point near each end. The hemispherical caps of the capsule should not be damaged in the process. This is important because the capsule or its cap acts as a sort of valve. Due to the pressure conditions, the capsule is pulled against the inlet aperture against the air flowing in and partly closes off this aperture. As the user continues to suck on the mouthpiece, a vacuum is produced in the capsule chamber by means of which the capsule is drawn towards the air outlet along with the incoming air. The vacuum now produced at the air inlet causes the capsule to be drawn towards the inlet aperture again. The entire procedure is repeated in rapid succession as long as the user continues to inhale through the mouthpiece, and this causes the capsule to vibrate strongly.

The capsule may be opened outside the inhaler. However, it is more convenient to mount cutting tools on the inhaler with which the capsule can be opened inside the chamber.

The invention can perhaps be better understood by making reference to the drawings:

The embodiment of the inhaler according to the invention shown in FIG. 1 consists of lower part 1 and mouthpiece 2, which are fitted together. The lower part 1 contains air inlet channel 3 and a cutting mechanism 4, which is held in its normal position by a spring element 5. The mouthpiece 2 contains capsule chamber 6. Projections 7, which limit the clearance of a capsule 15, project into the extension 6a of the capsule chamber 6. A perforated plate 8 prevents any fragments of capsule 15, for example, from being inhaled.

The inhaler can be compressed axially counter to the pressure of a spring element 9, whereupon the upper edge of the lower part 1 reaches position 10. In this position blades or points 11 of the cutting mechanism 4 are able to penetrate through openings 12 into the capsule chamber 6 and open a capsule 15 fixed therein.

Figure 2:
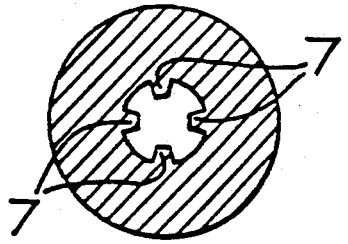
FIG. 2 represents a cross-sectional view along the line A—A in FIG. 1.

FIG. 2 shows the capsule chamber extension 6a with the projections 7 which limit the play of the capsule 15 of the actual capsule chamber 6.

Figure 3:
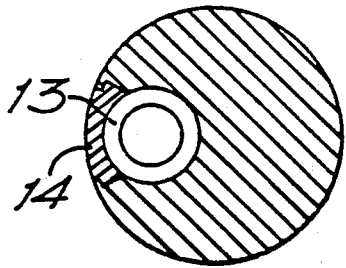
FIG. 3 represents a cross-sectional view of an embodiment of the invention in which the chamber is laterally mounted and can be opened and closed by means of a movable plate.

FIG. 3 shows a laterally mounted capsule chamber 13 and an axially movable element 14 which serves to open and close capsule chamber 13 and simultaneously forms part of the side wall.

In order to use the inhaler as shown in FIG. 1, the lower part 1 and mouthpiece 2 are pulled apart, the capsule 15 is inserted, and the two parts 1 and 2 of the inhaler are fitted together. After mouthpiece 2 has been pushed inwards against lower part 1 into position 10 counter to the spring element 9, the cutting mechanism 4 is actuated and then released. The inhaler returns to the position shown in FIG. 1 under pressure from the spring element 9. Inhalation then takes place by breathing in through the mouthpiece 2.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. An inhaler for inhalation of a powdered pharmaceutical composition from a pierceable capsule having a cylindrical side wall and hemispherical ends, said inhaler comprising a mouthpiece portion having a first end adapted for connection to a user, an opposite second end and an axis extending therebetween and a base portion having a first end, an opposite second end and an axis extending therebetween, said second end of said base portion being slidably connected over the second end of said mouthpiece portion such that the portions are in coaxial alignment and are axially slidable with respect to one another from a use position to a capsule piercing position wherein the distance between the first ends of the portions is less than the distance between the first ends of the portions in the use position, said inhaler further including means for normally biasing the portions in the use position but permitting the portions to be slid to the piercing position, said portions defining, in combination, a substantially coaxial cylindrical capsule chamber for receiving the capsule having opposite ends, an internal width in the use position, which is sized to be less than the length of the capsule and an internal length, in the use position, which is sized to be about 1.02 to 2 times the length of the capsule, said base portion defining an air inlet passage terminating in one end of said capsule chamber and the mouthpiece portion defining an air outlet passage fluidically communicating with the other end of said capsule chamber, the internal cross-section of the air inlet passage being smaller than the internal cross-section of said air outlet passage which is itself smaller than the internal width of the capsule chamber, said capsule chamber being coaxially aligned with said air inlet and air outlet passages, said mouthpiece portion defining apertures extending into said capsule chamber between said opposite ends, said apertures being located to be between the first and second ends of the base portion in the piercing position and said base portion including means therein, between said first and second ends, for aligning with said apertures and piercing, via said apertures, the cylindrical side wall of the capsule when said portions are in the capsule piercing position.

2. An inhaler of claim 1, wherein the diameter of the capsule chamber, in the use position, is sized to be about 1.2 to 1.6 times the diameter of the capsule and the length of the capsule chamber, in the use position, is sized to be about 1.1 to 1.6 times the length of the capsule.

3. An inhaler of claim 1, further including a pierceable capsule containing a micronized pharmaceutical composition to be inhaled received in the capsule chamber.

* * * * *